United States Patent
Plews

(10) Patent No.: US 12,194,136 B2
(45) Date of Patent: Jan. 14, 2025

(54) METHOD OF TREATING HAIR LOSS AND FORMULATION FOR TREATMENT

(71) Applicant: ELEVAI Labs, Inc., Newport Beach, CA (US)

(72) Inventor: Jordan Robert Plews, Sacramento, CA (US)

( * ) Notice: Subject to any disclaimer, the term of this patent is extended or adjusted under 35 U.S.C. 154(b) by 0 days.

(21) Appl. No.: 18/101,974

(22) Filed: Jan. 26, 2023

(65) Prior Publication Data

US 2023/0172838 A1 Jun. 8, 2023

Related U.S. Application Data

(63) Continuation-in-part of application No. 17/865,229, filed on Jul. 14, 2022, now Pat. No. 11,878,038.

(60) Provisional application No. 63/256,593, filed on Oct. 17, 2021.

(51) Int. Cl.
*A61K 8/98* (2006.01)
*A61Q 7/00* (2006.01)

(52) U.S. Cl.
CPC .............. *A61K 8/981* (2013.01); *A61Q 7/00* (2013.01)

(58) Field of Classification Search
CPC .................................. A61K 8/981; A61Q 7/00
See application file for complete search history.

(56) References Cited

U.S. PATENT DOCUMENTS

| | | | |
|---|---|---|---|
| 9,119,974 B2 * | 9/2015 | Al-Qahtani | A61K 8/985 |
| 2013/0209528 A1 * | 8/2013 | Levi | A61K 8/981 |
| | | | 424/520 |
| 2018/0318356 A1 * | 11/2018 | Pettine | A61K 35/28 |

OTHER PUBLICATIONS

UL Prospector webpage detailing Bis(Tripeptide-1) Copper Acetate, downloaded Mar. 21, 2024 from https://www.ulprospector.com/en/na/PersonalCare/Detail/5738/702677/SpecPed-GCu21P-Copper-Tripeptide; downloaded Mar. 21, 2024; available on the internet Dec. 14, 2016 (Year: 2016).*

* cited by examiner

*Primary Examiner* — Michael P Cohen
(74) *Attorney, Agent, or Firm* — Josiah Barbour

(57) ABSTRACT

A method, and formulations for the method, for the treatment of hair loss is herein described. Typically, the method involves applying an exosome-based skincare product to skin affected by hair loss, such as the skin of the scalp. The exosome-based skincare product contains exosomes produced by and excreted from human umbilical mesenchymal stem cells cultured in vitro under specific conditions and then contained within a solvent. The hair loss may be caused by androgenic alopecia, alopecia areta, or telogen effulvium.

10 Claims, No Drawings

METHOD OF TREATING HAIR LOSS AND FORMULATION FOR TREATMENT

CROSS-REFERENCE TO RELATED APPLICATIONS

This application is a continuation-in-part of U.S. patent application Ser. No. 17/865,229, filed Jul. 14, 2022, and titled "Exosome-based Skincare Product" which claims priority to U.S. Provisional Patent Application Ser. No. 63/256,593, filed Oct. 17, 2021, and titled "Exosome-based Skincare Product"; the contents of which are hereby incorporated by reference.

BACKGROUND

Field of the Invention

The present invention relates generally to treatments for hair loss along with products used to treat hair loss. More specifically, the present invention relates to exosome-based methods and products for treating hair loss.

Description of the Related Art

Current treatments for hair loss include medications, both nonprescription and prescription varieties, surgery, and laser therapy. The medications most commonly used inhibit 5α-reductase, an enzyme family involved in steroid metabolism. A common side effect of these medications is a decrease in the conversion of testosterone to dihydrotestosterone, which results in an increase in testosterone and estradiol. While increasing testosterone and estradiol in men is largely seen as medically inconsequential with 5α-reductase inhibition, increasing these hormones in women can have many unwanted consequences. As such, most of the medications currently available to patients with hair loss are contraindicated for use in women. Frequently, these medications require continued use retain any benefits from the medication. Some of the medications can result in unwanted hair growth on the skin, including the palms of the hands.

Surgical options for treatment of hair loss are available and are frequently successful. Multiple surgeries are frequently needed to achieve the desired end result, but for some individuals a single surgery will achieve the desired result. If the hair loss has genetic causes, hair loss will eventually progress despite surgery. This treatment is available for both men and women, as it has none of the underlying hormonal issues that currently available medications can cause. However, these surgeries are expensive and are typically not covered by insurance, leaving the patient to pay the entire cost for the surgery themselves. It is not unheard of for these surgeries to cost in excess of $20,000.

Laser therapy is a new treatment that has shown some improvement in hair density in both men and women. Only a few small studies have been performed and the long-term effects are unclear.

SUMMARY

In accordance with the embodiments herein, a method for treating hair loss, along with formulations for use, is described. The method comprises applying an exosome-based skincare product to skin where hair loss has occurred. The exosome-based skincare product contains exosomes produced by and excreted from human umbilical mesenchymal stem cells cultured in vitro under specific conditions and then contained within a solvent. Note that the exosome-based skincare product does not contain live human umbilical mesenchymal stem cells. Optional ingredients such as skin-conditioning agents, antioxidants, surfactants, buffering agents, viscosity decreasing agents, viscosity increasing agents, peptides, binders, and/or humectants may be included.

DETAILED DESCRIPTION OF EMBODIMENTS

In the following description, for purposes of explanation and not limitation, details and descriptions are set forth in order to provide a thorough understanding of the present invention. However, it will be apparent to those skilled in the art that the present invention may be practiced in other embodiments that depart from these details and descriptions without departing from the spirit and scope of the invention.

For the purpose of definition, within this document the term "media" is used to mean any substrate which can contain an exosome-based product and is not to be read as the plural form of "medium". Appropriate substrates for skincare are well known within the industry and as such are not discussed in detail herein.

For the purpose of definition, within this document, the term "human umbilical mesenchymal stem cells" is used to mean any preparation of human umbilical mesenchymal stem cells, including human umbilical mesenchymal stem cells contained within human umbilical stem cell conditioned media. Within the industry, human umbilical mesenchymal stem cells are known by a number of different names, including but not limited to human Wharton's Jelly derived mesenchymal stem cells, human Wharton's Jelly derived mesenchymal stromal cells, human umbilical derived mesenchymal stromal cells, hUMSCs, hWJMSCs, Wharton's Jelly derived multipotent progenitor cells, and umbilical derived multipotent progenitor cells. Additionally, these stem cells can be identified by cell surface markers, such as CD90+, CD105+, CD73+, and CD45−.

Within this document, the exosomes discussed are much smaller than a typical mesenchymal stem cell, about 1/100th the size of a cell, and have a diameter of approximately 30-150 nanometers (nm). Exosomes are roughly spherical and made up of a lipid bilayer produced by the cell they originated from. This lipid bilayer forms a protective 'shell' or outer casing, and within the 'shell' or outer casing is the exosome payload which contains molecules deposited there by the cell that generated the exosome. While exosomes are generated using some of the origin cell's own cellular material, the exosomes do not contain cells, nor are they explicitly cellular material.

In an illustrative embodiment of the invention, the method comprises the step of applying an exosome-based skincare product to skin where hair loss has occurred. The exosome-based skincare product contains exosomes in or derived from a media conditioned by human umbilical mesenchymal stem cells within a solvent. In optional embodiments, skin-conditioning agents, antioxidants, surfactants, buffering agents, viscosity decreasing agents, viscosity increasing agents, peptides, binders, and/or humectants may be included. Other optional ingredients are contemplated and described herein. Frequently, all of these optional ingredients are included with the human umbilical mesenchymal stem cell derived exosomes, or media, and solvent. Additional optional ingredients beyond those explicitly described herein are contemplated.

In most embodiments, the solvent is water. However, oil-based solvents are contemplated.

Skin-conditioning agents within the skincare industry are vast and well documented. Any of the well-known skin-conditioning agents work well with the invention and is contemplated. Specifically, glycerin, sodium hyaluronate, niacinamide, panthenol, *Caesalpinia spinosa* gum, ceramide NP, ceramide AP, ceramide EOP, yeast extract, *Citrullus ianatus* fruit extract, *Pyrus malus* fruit extract, *Lens esculenta* fruit extract, sodium PCA, caprylyl glycol, ethylhexylglycerin, hydrolyzed sodium hyaluronate, and phytosphingosine are frequently used with the invention.

As with skin-conditioning agents, antioxidants are well known and well documented. With the invention, the antioxidants most frequently used are ascorbic acid, magnesium ascorbyl phosphate, ascorbyl glucoside, sodium ascorbyl phosphate, tetrahexyldecyl ascorbate, glutathione, and *Camellia sinensis* leaf extract. Any other well-known antioxidants in the skincare industry can be and is contemplated.

Surfactants frequently used with the invention include polysorbate 20, polysorbate 60, and sodium lauroyl lactylate. Any other well-known surfactant in the skincare industry can be used and is contemplated. While not a surfactant itself, cholesterol is commonly used to stabilize the emulsions that are achieved with surfactants. Some embodiments of the exosome-based skincare product include cholesterol.

Buffering agents, such as sodium lactate, disodium phosphate, and sodium phosphate most frequently used with the invention, are common in the skincare industry. As many skincare products have harsh pH, both acidic and basic, buffers are frequently used to ensure that the final product is of a neutral pH for the skin. Other well-known buffering agents in the skincare industry are acceptable and are contemplated.

Viscosity increasing and decreasing agents are frequently used in the skincare industry. Those most frequently used with the invention are hydroxyethylcellulose, *Caesalpinia spinosa* gum, dextran, carbomer, hexylene glycol, and butylene glycol. Any other well-known viscosity increasing or decreasing agent in the skincare industry can be used and is contemplated.

Peptides are commonly added to skincare products. Peptides such as bis(tripeptide-1) copper acetate, acetyl octapeptide-3, palmitoyl tripeptide-37, palmitoyl pripeptide-1, palmitoyl tetrapeptide-7, acetyl hexapeptide-8, and trifluoroacetyl tripeptide-2 are most frequently used with the invention. Other peptides well-known in the skincare industry can be used and are contemplated.

Binders and bulking agents are frequently used in the skincare industry to improve the usability of a product for the consumer. Binders such as hydroxyethylcellulose, dextran, pullulan, and xanthan gum are the binders and bulking agents most frequently used. However, other binders and bulking agents are contemplated, especially those well-known within the skincare industry.

The benefits of *Aloe barbadensis* leaf juice for the skin are well studied, well known, and well documented. Some embodiments include *Aloe barbadensis* leaf juice for its skincare related properties.

Humectants are frequently used in the skincare industry to prevent the loss of moisture from the skin. Glycerin, sodium hyaluronate, arginine in all of its forms, *Nannochloropsis oculate* extract, sodium PCA, and hydrolyzed sodium hyaluronate are the most common humectants used. Other humectants well-known within the skincare industry are contemplated.

Antimicrobials, such as *Leuconostoc* root ferment filtrate most commonly used, are vitally important to the skincare industry. Other antimicrobials are contemplated, especially those well-known in the skincare industry.

Chelating agents are commonly used within the skincare industry to stabilize the metal ions found in many skincare products. For the exosome-based skincare product, sodium phytate is the most frequently used chelating agent. Other chelating agents, such as ethylenediaminetetraacetic acid, etidronic acid, galactaric acid, sodium metasilicate, and phosphate derivatives, as well as derivatives of each of the previously listed acids, are also used in some embodiments. Other chelating agents known within the skincare industry are contemplated.

Preservatives, such as phenoxyethanol, sodium benzoate, and potassium sorbate, are key to preserving the life of skincare products. Other preservatives, especially those known in the skincare industry, are contemplated.

In another illustrative embodiment the exosome-based skincare product contains human umbilical mesenchymal stem cell conditioned media between 25.0 and 50.0 percent by mass, water between 0.1 and 60.0 percent by mass, glycerin between 3.0 and 10.0 percent by mass, *Aloe barbadensis* leaf juice between 1.0 and 5.0 percent by mass, sodium hyaluronate between 1.0 and 5.0 percent by mass, niacinamide between 1.0 and 5.0 percent by mass, panthenol between 1.0 and 5.0 percent by mass, magnesium ascorbyl phosphate between 1.0 and 5.0 percent by mass, ascorbyl glucoside between 0.5 and 3.0 percent by mass, sodium ascorbyl phosphate between 0.1 and 3.0 percent by mass, hydroxyethylcellulose between 0.1 and 5.0 percent by mass, *Caesalpinia spinosa* gum between 0.1 and 3.0 percent by mass, bis(tripeptide-1) copper acetate between 0.1 and 5.0 percent by mass, polysorbate 20 between 0.1 and 3.0 percent by mass, polysorbate 60 between 0.1 and 3.0 percent by mass, ceramide NP between 0.1 and 3.0 percent by mass, ceramide AP between 0.1 and 3.0 percent by mass, ceramide EOP between 0.1 and 3.0 percent by mass, acetyl octapeptide-3 between 0.1 and 3.0 percent by mass, palmitoyl tripeptide-37 between 0.1 and 3.0 percent by mass, palmitoyl tripeptide-1 between 0.1 and 3.0 percent by mass, palmitoyl tetrapeptide-7 between 0.1 and 3.0 percent by mass, acetyl hexapeptide-8 between 0.1 and 3.0 percent by mass, trifluoroacetyl tripeptide-2 between 0.1 and 3.0 percent by mass, dextran between 0.1 and 3.0 percent by mass, tetrahexyldecyl ascorbate between 0.1 and 10.0 percent by mass, pullulan between 0.1 and 3.0 percent by mass, arginine between 0.1 and 2.0 percent by mass, glutathione between 0.1 and 2.0 percent by mass, yeast extract between 0.1 and 3.0 percent by mass, *Nannochloropsis oculata* extract between 0.1 and 3.0 percent by mass, *Camellia sinensis* leaf extract between 0.1 and 3.0 percent by mass, *Citrullus lanatus* fruit extract between 0.1 and 3.0 percent by mass, *Pyrus malus* fruit extract between 0.1 and 3.0 percent by mass, *Lens esculenta* fruit extract between 0.1 and 3.0 percent by mass, sodium PCA between 0.1 and 3.0 percent by mass, sodium lactate between 0.1 and 3.0 percent by mass, sodium phytate between 0.1 and 3.0 percent by mass, *Leuconostoc* root ferment filtrate between 0.1 and 3.0 percent by mass, caprylyl glycol between 0.1 and 3.0 percent by mass, ethylhexylglycerin between 0.1 and 3.0 percent by mass, phytosphingosine between 0.1 and 3.0 percent by mass, cholesterol between 0.1 and 3.0 percent by mass, sodium lauroyl lactylate between 0.1 and 3.0 percent by mass, carbomer between 0.1 and 3.0 percent by mass, xanthan gum between 0.1 and 3.0 percent by mass, phenoxyethanol between 0.5 and 3.0 percent by mass, hexylene glycol between 0.1 and 1.0 percent by mass, butylene glycol between 0.1 and 1.0 percent by mass, disodium phosphate between 0.1 and 1.0 percent by mass, sodium phosphate between 0.1 and 1.0 percent by mass, sodium benzoate between 0.1 and 1.0 percent by mass, and potassium sorbate between 0.1 and 1.0 percent by mass.

In a further illustrative embodiment the exosome-based skincare product contains human umbilical mesenchymal stem cell conditioned media between 10.0 and 55.0 percent by mass, water between 1.0 and 30.0 percent by mass, glycerin between 0.1 and 5.0 percent by mass, *Aloe barbadensis* leaf juice between 0.1 and 5.0 percent by mass, hydroxyethylcellulose between 0.1 and 5.0 percent by mass, hydrolyzed sodium hyaluronate between 0.1 and 5.0 percent by mass, sodium hyaluronate between 1.0 and 5.0 percent by mass, bis(tripeptide-1) copper acetate between 0.1 and 5.0 percent by mass, polysorbate 20 between 0.1 and 3.0 percent by mass, polysorbate 60 between 0.1 and 3.0 percent by mass, ceramide NP between 0.1 and 5.0 percent by mass, ceramide AP between 0.1 and 5.0 percent by mass, ceramide EOP between 0.1 and 5.0 percent by mass, acetyl octapeptide-3 between 0.1 and 5.0 percent by mass, palmitoyl tripeptide-37 between 0.1 and 5.0 percent by mass, palmitoyl tripeptide-1 between 0.1 and 5.0 percent by mass, palmitoyl tetrapeptide-7 between 0.1 and 5.0 percent by mass, acetyl hexapeptide-8 between 0.1 and 5.0 percent by mass, trifluoroacetyl tripeptide-2 between 0.1 and 5.0 percent by mass, dextran between 0.1 and 5.0 percent by mass, pullulan between 0.1 and 3.0 percent by mass, arginine between 0.1 and 3.0 percent by mass, glutathione between 0.1 and 3.0 percent by mass, yeast extract between 0.1 and 3.0 percent by mass, *Nannochloropsis oculata* extract between 0.1 and 3.0 percent by mass, *Camellia sinensis* leaf extract between 0.1 and 3.0 percent by mass, *Citrullus lanatus* fruit extract between 0.1 and 3.0 percent by mass, *Pyrus malus* fruit extract between 0.1 and 3.0 percent by mass, *Lens esculenta* fruit extract between 0.1 and 3.0 percent by mass, sodium PCA between 0.1 and 3.0 percent by mass, sodium lactate between 0.1 and 3.0 percent by mass, sodium phytate between 0.1 and 3.0 percent by mass, *Leuconostoc* root ferment filtrate between 0.1 and 3.0 percent by mass, caprylyl glycol between 0.1 and 3.0 percent by mass, ethylhexylglycerin between 0.1 and 3.0 percent by mass, phytosphingosine between 0.1 and 3.0 percent by mass, cholesterol between 0.1 and 3.0 percent by mass, sodium lauroyl lactylate between 0.1 and 3.0 percent by mass, carbomer between 0.1 and 3.0 percent by mass, xanthan gum between 0.1 and 3.0 percent by mass, phenoxyethanol between 0.5 and 3.0 percent by mass, hexylene glycol between 0.1 and 1.0 percent by mass, butylene glycol between 0.1 and 1.0 percent by mass, disodium phosphate between 0.1 and 1.0 percent by mass, sodium phosphate between 0.1 and 1.0 percent by mass, sodium benzoate between 0.1 and 1.0 percent by mass, and potassium sorbate between 0.1 and 1.0 percent by mass.

The most frequent embodiment of the invention will be to treat hair loss on the scalp. Treating hair loss on the face, such as eye lashes, eyebrows, beard, or mustache, is also possible using this invention.

The hair loss may be as a result of androgenic alopecia, alopecia areta, or telogen effluvium. The hair loss may be in male or female patients, as the treatment works on with both sexes.

What is claimed is:

1. A method, comprising:
 applying an exosome-based skincare product to skin that has hair loss;
 wherein the exosome-based skincare product comprises:
  exosomes created by human umbilical mesenchymal stem cells wherein the exosomes are between 25.0 and 50.0 percent by mass;
  water between 0.1 and 60.0 percent by mass;
  glycerin between 3.0 and 10.0 percent by mass;
  *Aloe barbadensis* leaf juice between 1.0 and 5.0 percent by mass;
  sodium hyaluronate between 1.0 and 5.0 percent by mass;
  niacinamide between 1.0 and 5.0 percent by mass;
  panthenol between 1.0 and 5.0 percent by mass;
  magnesium ascorbyl phosphate between 1.0 and 5.0 percent by mass;
  ascorbyl glucoside between 0.5 and 3.0 percent by mass;
  sodium ascorbyl phosphate between 0.1 and 3.0 percent by mass;
  hydroxyethylcellulose between 0.1 and 5.0 percent by mass;
  *Caesalpinia spinosa* gum between 0.1 and 3.0 percent by mass;
  bis(tripeptide-1) copper acetate between 0.1 and 5.0 percent by mass;
  polysorbate 20 between 0.1 and 3.0 percent by mass;
  polysorbate 60 between 0.1 and 3.0 percent by mass;
  ceramide NP between 0.1 and 3.0 percent by mass;
  ceramide AP between 0.1 and 3.0 percent by mass;
  ceramide EOP between 0.1 and 3.0 percent by mass;
  acetyl octapeptide-3 between 0.1 and 3.0 percent by mass;
  palmitoyl tripeptide-37 between 0.1 and 3.0 percent by mass;
  palmitoyl tripeptide-1 between 0.1 and 3.0 percent by mass;
  palmitoyl tetrapeptide-7 between 0.1 and 3.0 percent by mass;
  acetyl hexapeptide-8 between 0.1 and 3.0 percent by mass;
  trifluoroacetyl tripeptide-2 between 0.1 and 3.0 percent by mass;
  dextran between 0.1 and 3.0 percent by mass;
  tetrahexyldecyl ascorbate between 0.1 and 10.0 percent by mass;
  pullulan between 0.1 and 3.0 percent by mass;
  arginine between 0.1 and 2.0 percent by mass;
  glutathione between 0.1 and 2.0 percent by mass;
  yeast extract between 0.1 and 3.0 percent by mass;
  *Nannochloropsis oculata* extract between 0.1 and 3.0 percent by mass;
  *Camellia sinensis* leaf extract between 0.1 and 3.0 percent by mass;
  *Citrullus lanatus* fruit extract between 0.1 and 3.0 percent by mass;
  *Pyrus malus* fruit extract between 0.1 and 3.0 percent by mass;
  *Lens esculenta* fruit extract between 0.1 and 3.0 percent by mass;
  sodium pyrrolidone carboxylate (sodium PCA) between 0.1 and 3.0 percent by mass;
  sodium lactate between 0.1 and 3.0 percent by mass;
  sodium phytate between 0.1 and 3.0 percent by mass;
  *Leuconostoc* root ferment filtrate between 0.1 and 3.0 percent by mass;
  caprylyl glycol between 0.1 and 3.0 percent by mass;
  ethylhexylglycerin between 0.1 and 3.0 percent by mass;
  phytosphingosine between 0.1 and 3.0 percent by mass;
  cholesterol between 0.1 and 3.0 percent by mass;
  sodium lauroyl lactylate between 0.1 and 3.0 percent by mass;

carbomer between 0.1 and 3.0 percent by mass;
xanthan gum between 0.1 and 3.0 percent by mass;
phenoxyethanol between 0.5 and 3.0 percent by mass;
hexylene glycol between 0.1 and 1.0 percent by mass;
butylene glycol between 0.1 and 1.0 percent by mass;
disodium phosphate between 0.1 and 1.0 percent by mass;
sodium phosphate between 0.1 and 1.0 percent by mass;
sodium benzoate between 0.1 and 1.0 percent by mass; and
potassium sorbate between 0.1 and 1.0 percent by mass.

2. The method of claim 1, wherein the skin is facial skin.

3. The method of claim 2, wherein the hair loss has occurred in areas of the face selected from eye lashes, eyebrows, beard, and mustache.

4. The method of claim 1, wherein the skin is scalp skin.

5. The method of claim 1, wherein the hair loss is caused by a disorder selected from the group consisting of androgenic alopecia, alopecia areta, and telogen effulvium.

6. A method, comprising:
applying an exosome-based skincare product to skin that has hair loss;
wherein the exosome-based skincare product comprises:
exosomes created by human umbilical mesenchymal stem cell wherein the exosomes are between 10.0 and 55.0 percent by mass;
water between 1.0 and 30.0 percent by mass;
glycerin between 0.1 and 5.0 percent by mass;
*Aloe barbadensis* leaf juice between 0.1 and 5.0 percent by mass;
hydroxyethylcellulose between 0.1 and 5.0 percent by mass;
hydrolyzed sodium hyaluronate between 0.1 and 5.0 percent by mass;
sodium hyaluronate between 1.0 and 5.0 percent by mass;
bis(tripeptide-1) copper acetate between 0.1 and 5.0 percent by mass;
polysorbate 20 between 0.1 and 3.0 percent by mass;
polysorbate 60 between 0.1 and 3.0 percent by mass;
ceramide NP between 0.1 and 5.0 percent by mass;
ceramide AP between 0.1 and 5.0 percent by mass;
ceramide EOP between 0.1 and 5.0 percent by mass;
acetyl octapeptide-3 between 0.1 and 5.0 percent by mass;
palmitoyl tripeptide-37 between 0.1 and 5.0 percent by mass;
palmitoyl tripeptide-1 between 0.1 and 5.0 percent by mass;
palmitoyl tetrapeptide-7 between 0.1 and 5.0 percent by mass;
acetyl hexapeptide-8 between 0.1 and 5.0 percent by mass;
trifluoroacetyl tripeptide-2 between 0.1 and 5.0 percent by mass;
dextran between 0.1 and 5.0 percent by mass;
pullulan between 0.1 and 3.0 percent by mass;
arginine between 0.1 and 3.0 percent by mass;
glutathione between 0.1 and 3.0 percent by mass;
yeast extract between 0.1 and 3.0 percent by mass;
*Nannochloropsis oculata* extract between 0.1 and 3.0 percent by mass;
*Camellia sinensis* leaf extract between 0.1 and 3.0 percent by mass;
*Citrullus lanatus* fruit extract between 0.1 and 3.0 percent by mass;
*Pyrus malus* fruit extract between 0.1 and 3.0 percent by mass;
*Lens esculenta* fruit extract between 0.1 and 3.0 percent by mass;
sodium pyrrolidone carboxylate (sodium PCA) between 0.1 and 3.0 percent by mass;
sodium lactate between 0.1 and 3.0 percent by mass;
sodium phytate between 0.1 and 3.0 percent by mass;
*Leuconostoc* root ferment filtrate between 0.1 and 3.0 percent by mass;
caprylyl glycol between 0.1 and 3.0 percent by mass;
ethylhexylglycerin between 0.1 and 3.0 percent by mass;
phytosphingosine between 0.1 and 3.0 percent by mass;
cholesterol between 0.1 and 3.0 percent by mass;
sodium lauroyl lactylate between 0.1 and 3.0 percent by mass;
carbomer between 0.1 and 3.0 percent by mass;
xanthan gum between 0.1 and 3.0 percent by mass;
phenoxyethanol between 0.5 and 3.0 percent by mass;
hexylene glycol between 0.1 and 1.0 percent by mass;
butylene glycol between 0.1 and 1.0 percent by mass;
disodium phosphate between 0.1 and 1.0 percent by mass;
sodium phosphate between 0.1 and 1.0 percent by mass;
sodium benzoate between 0.1 and 1.0 percent by mass; and
potassium sorbate between 0.1 and 1.0 percent by mass.

7. The method of claim 6, wherein the skin is facial skin.

8. The method of claim 7, wherein the hair loss has occurred in areas of the face selected from eye lashes, eyebrows, beard, and mustache.

9. The method of claim 6, wherein the skin is scalp skin.

10. The method of claim 6, wherein the hair loss is caused by a disorder selected from the group consisting of androgenic alopecia, alopecia areta, and telogen effulvium.

* * * * *